(12) United States Patent
Rintamäki et al.

(10) Patent No.: US 11,375,967 B2
(45) Date of Patent: Jul. 5, 2022

(54) AUTOMATIC PROTOCOL SELECTION FOR AN IMAGING DEVICE

(71) Applicant: PaloDEx Group OY, Tuusula (FI)

(72) Inventors: Markus Kristian Rintamäki, Tuusula (FI); Esa Suuronen, Kerava (FI)

(73) Assignee: PaloDEx Group OY, Tuusula (FI)

( * ) Notice: Subject to any disclaimer, the term of this patent is extended or adjusted under 35 U.S.C. 154(b) by 0 days.

(21) Appl. No.: 15/462,399

(22) Filed: Mar. 17, 2017

(65) Prior Publication Data
US 2018/0263583 A1 Sep. 20, 2018

(51) Int. Cl.
| | |
|---|---|
| *A61B 6/14* | (2006.01) |
| *A61B 6/00* | (2006.01) |
| *G16H 40/63* | (2018.01) |
| *G16H 40/67* | (2018.01) |
| *A61B 6/03* | (2006.01) |
| *A61C 9/00* | (2006.01) |
| *G06F 3/04842* | (2022.01) |
| *G06F 3/04847* | (2022.01) |

(52) U.S. Cl.
CPC .............. *A61B 6/469* (2013.01); *A61B 6/032* (2013.01); *A61B 6/14* (2013.01); *A61B 6/545* (2013.01); *A61B 6/563* (2013.01); *A61C 9/0053* (2013.01); *G16H 40/63* (2018.01); *G16H 40/67* (2018.01); *G06F 3/04842* (2013.01); *G06F 3/04847* (2013.01)

(58) Field of Classification Search
CPC .......... A61B 6/469; A61B 6/032; A61B 6/14; A61B 6/545; A61B 6/563; A61C 9/0053; G16H 40/60; G06F 3/04842; G06F 3/04847
See application file for complete search history.

(56) References Cited

U.S. PATENT DOCUMENTS

| | | | |
|---|---|---|---|
| 5,692,027 A | 11/1997 | Yoshimura et al. | |
| 8,712,798 B2 | 4/2014 | Gotman et al. | |
| 2005/0267348 A1* | 12/2005 | Wollenweber | A61B 6/032 600/407 |
| 2007/0081703 A1 | 4/2007 | Johnson | |
| 2011/0064188 A1 | 3/2011 | Suzuki et al. | |

(Continued)

FOREIGN PATENT DOCUMENTS

| | | |
|---|---|---|
| CN | 104546151 A | 4/2015 |
| JP | 2011152411 | 8/2011 |
| JP | 2014-193193 A | 10/2014 |

OTHER PUBLICATIONS

European Patent Office Search Report for Application No. 18161652.5 dated Jul. 10, 2018, 7 pages.

(Continued)

*Primary Examiner* — Jennifer N Welch
*Assistant Examiner* — Amy P Hoang
(74) *Attorney, Agent, or Firm* — Michael Best & Friedrich LLP

(57) ABSTRACT

A method of automatically determining an imaging protocol. The method includes receiving, via a user-interface, a scan request. The scan request includes a region-of-interest definition. The method further includes determining, via a controller, an imaging protocol based on the scan request, and performing, via an imaging device, a scan of a patient based on the imaging protocol.

21 Claims, 6 Drawing Sheets

(56) References Cited

U.S. PATENT DOCUMENTS

| | | | | |
|---|---|---|---|---|
| 2013/0090946 A1* | 4/2013 | Foo | ........................ | G06Q 10/06 |
| | | | | 705/3 |
| 2014/0126686 A1* | 5/2014 | Sadakane | ............... | A61B 6/145 |
| | | | | 378/13 |
| 2014/0226885 A1 | 8/2014 | Keating et al. | | |
| 2014/0328446 A1 | 11/2014 | Sugihara et al. | | |
| 2015/0085971 A1* | 3/2015 | Braun | .................... | A61B 6/032 |
| | | | | 378/8 |
| 2015/0164446 A1* | 6/2015 | Toimela | .................. | A61B 6/14 |
| | | | | 378/39 |
| 2016/0220844 A1 | 8/2016 | Paysan et al. | | |
| 2017/0135654 A1 | 5/2017 | Van Daal et al. | | |
| 2018/0144823 A1* | 5/2018 | Raman | .................. | G16H 40/67 |

OTHER PUBLICATIONS

Japanese Patent Office Action for Application No. 2018-0450677, dated Feb. 27, 2019, with English translation, 7 pages.
Korean Patent Office Action for Application No. 10-2018-0029116 dated Jun. 24, 2019 (12 pages, English translation included).
Notice of Reason for Rejection issued by the Japan Patent Office for related Application No. 2018-050677 dated Oct. 29, 2019 (9 pages including English Translation).
Korean Patent Office Action for Application No. 10-2018-0029116 dated Feb. 27, 2020 (11 pages, English translation included).
European Patent Office Action for Application No. 18161652.5 dated Feb. 25, 2020 (4 pages).
Japanese Patent Office Action for Application No. 2018-050677 dated Jun. 24, 2020 (4 pages, English translation included).
Chinese Patent Office Action for Application No. 201810218861.5 dated Apr. 27, 2021 (17 pages, English translation included).
Israel Patent Office Action for Application No. 258141 dated Jun. 22, 2021 (4 pages with English language translation).
Chinese Office Action for Application No. 201810218861.5 dated Oct. 26, 2021 (10 pages with English translation).
Chinese Patent Office Action for Application No. 201810218861.5 dated Apr. 6, 2022 (9 pages including English summary).

* cited by examiner

AUTOMATIC PROTOCOL SELECTION FOR AN IMAGING DEVICE

TECHNICAL FIELD

Embodiments relate to dental imaging.

SUMMARY

Typically, a dental image of a patient is initially requested by a dentist. Often times, such a request is made manually (for example, orally or in writing). An operator then performs the imaging of the patient based on the request. The imaging of the patient is performed manually by the operator, and is mainly based on the know-how of the operator. Such a procedure can lead to mistakes and/or errors in the imaging of the patient.

Thus, in one embodiment, the invention provides a method of automatically determining an imaging protocol. The method includes receiving, via a user-interface, a scan request. The scan request includes a region-of-interest definition. The method further includes determining, via a controller and based on the scan request, at least one selected from the group consisting of an imaging protocol and an imaging parameter; and performing, via an imaging device, a scan of a patient based on the imaging protocol.

In another embodiment the invention provides an imaging system including a user-interface, a controller, and an imaging device. The controller includes a processor and a memory, the controller is configured to receive, from the user-interface, a scan request. The scan request includes a region-of-interest definition. The controller is further configured to determine, based on the scan request, at least one selected from the group consisting of an imaging protocol and an imaging parameter. The imaging device is configured to perform a scan of a patient based on the imaging protocol.

Other aspects of various embodiments will become apparent by consideration of the detailed description and accompanying drawings.

DETAILED DESCRIPTION

Before any embodiments are explained in detail, it is to be understood that these embodiments are not limited in their application to the details of construction and the arrangement of components set forth in the following description or illustrated in the following drawings. Other embodiments are possible and the embodiments described are capable being practiced or of being carried out in various ways.

Figure 1:
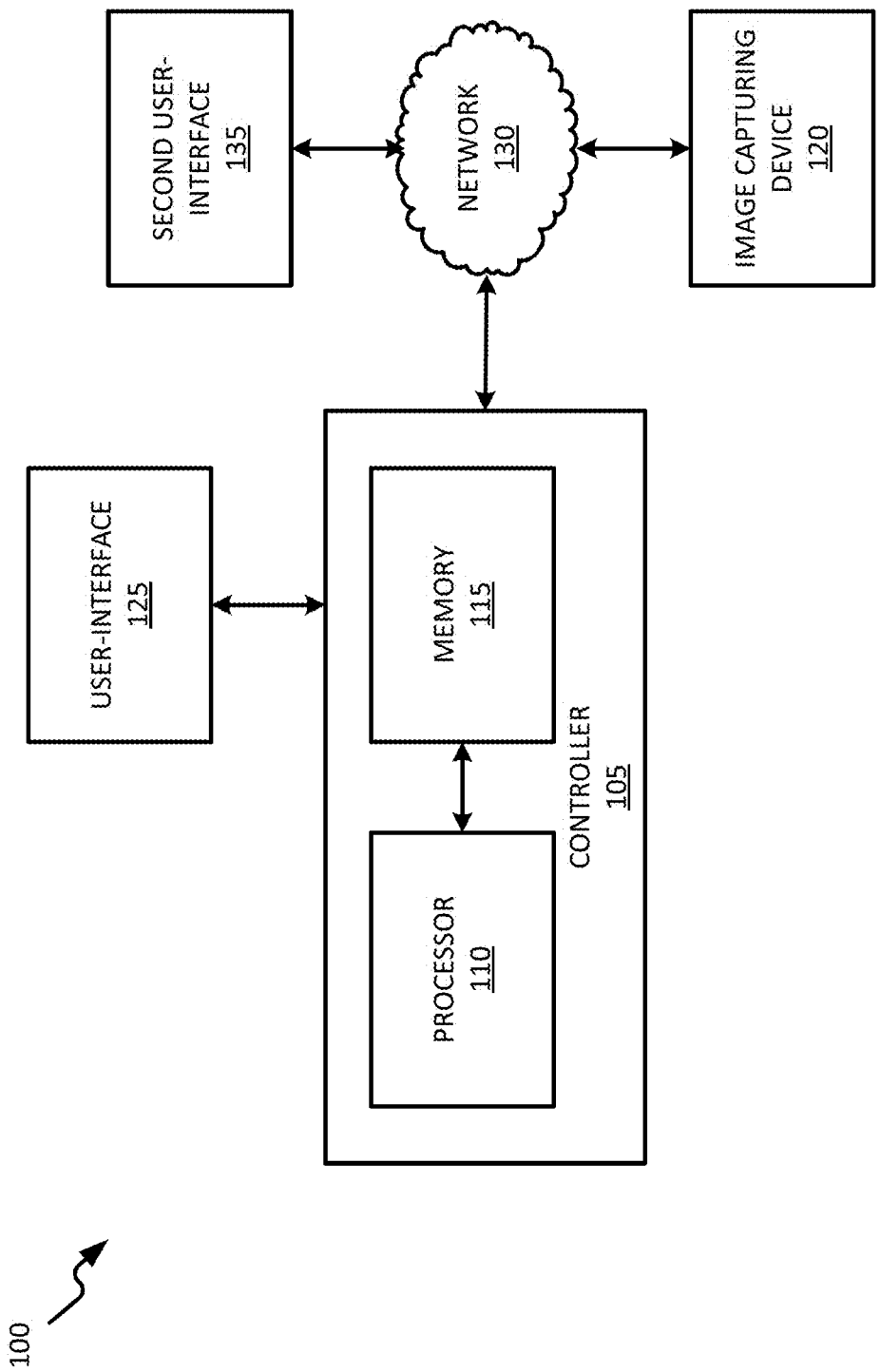
FIG. 1 is a block diagram illustrating an imaging system according to some embodiments.

FIG. 1 illustrates an imaging system 100 for capturing, processing, and analyzing dental imaging scans. In the example shown, the system 100 includes a controller 105 having an electronic processor 110 and a memory 115. The memory 115 stores instructions executable by the processor 110. In some instances, the controller 105 includes, for example, one or more of a microprocessor, digital signal processor (DSP), and field programmable gate array (FPGA), application specific integrated circuit (ASIC).

The controller 105 is electrically and/or communicatively coupled to an image capture device 120, a first user-interface 125, and a network 130. The image capture device 120 may be an x-ray imaging device, a computer tomography (CT) scanner, an optical surface scanner, or any other type of imaging modality scanner or imaging device configured to capture two-dimensional and/or three-dimensional images. Images captured by the image capture device 120 may be stored in memory 115 for, among other things, analysis and manipulation. Depending on the imaging modality, these digital renderings can include two or three dimensional geometrical data as well as other information including, for example, color, shade, and texture.

In the illustrated embodiment, the image capture device 120 is communicatively coupled to the controller 105 via network 130. In such an embodiment, the image capture device 120 may be located remotely from the controller 105. In other embodiments, the imaging capturing device 120 may be located proximate the controller 105 and a communicative connection between the image capture device 120 and the controller 105 need not be through network 130. In yet another embodiment, the controller 105 may be embedded within the image capture device 120.

The user-interface 125 receives input from a user and/or provides information to the user. The user-interface 125 may include one or more of the following: a display (for example, a liquid crystal display (LCD)); one or more light emitting diodes (LEDs) or other illumination devices; one or more input devices (for example, a keyboard, a mouse, a touch screen, a camera, a microphone, etc.); speakers for audible feedback (e.g., audible sounds, computer-generated voice messages, etc.); tactile feedback devices , for example, vibration devices that cause vibration; or other feedback devices.

The network 130 may be a local area network, a wide area network, or a combination of connections provided by such networks. All or part of the network 130 may be implemented via the Internet. In some embodiments, a second user-interface 135 may be communicatively coupled to the controller 105 via the network 130. In such an embodiment, the second user-interface 135 may be substantially similar to, and configured to perform similar functions as, the first user-interface 125. Furthermore, in some embodiments, the controller 105, image capture device 120, first user-interface 125, and second user-interface 135 are communicatively coupled to each other through the network 130. In yet another embodiments, the first user-interface 125 or the second user-interface 135 may be embedded within the image capture device 120. In some embodiments, additional user-interfaces, beyond the first user-interface 125 and the second user-interface 135, may be used.

Figure 2:
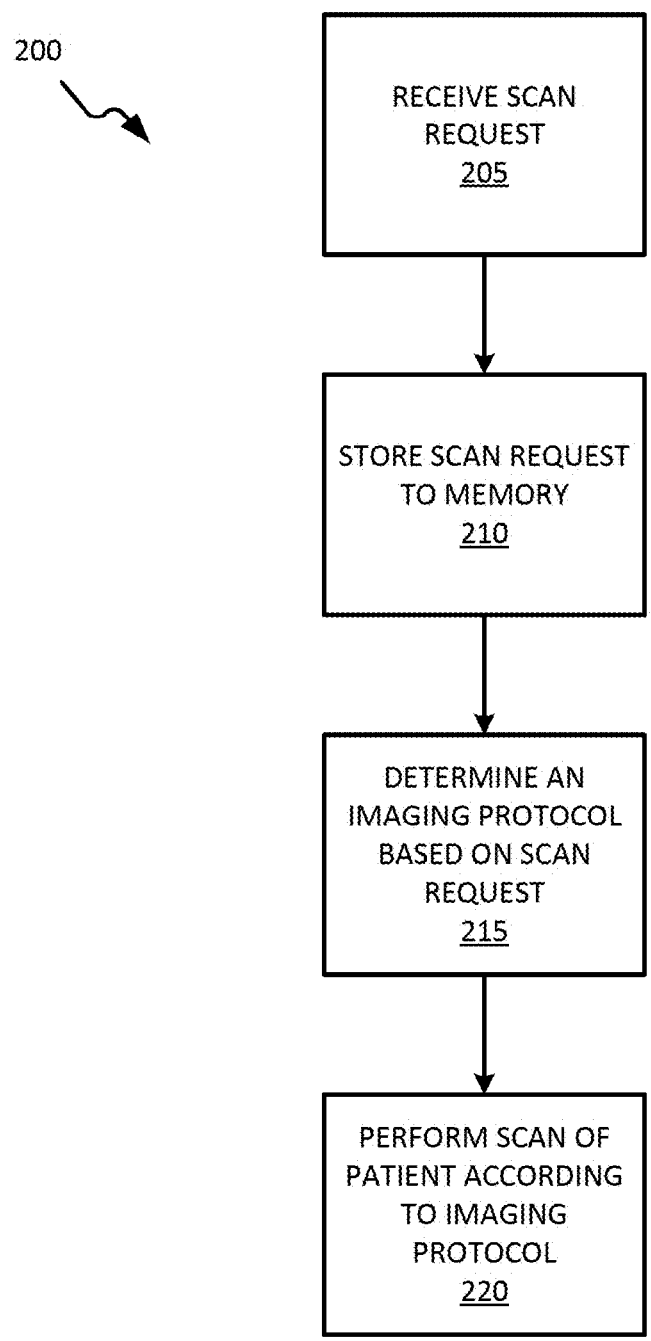
FIG. 2 is a flow chart illustrating a process of the system of FIG. 1 according to some embodiments.

FIG. 2 illustrates a process, or operation, 200 of the system 100 according to some embodiments. It should be understood that the order of the steps disclosed in process 200 could vary. Although illustrated as occurring in parallel order, in other embodiments, the steps disclosed may be performed in serial order. Furthermore, additional steps may be added to the process and not all of the steps may be required. A first user (for example, a dentist) initiates a scan, or acquisition, request (block 205).

Figure 3:
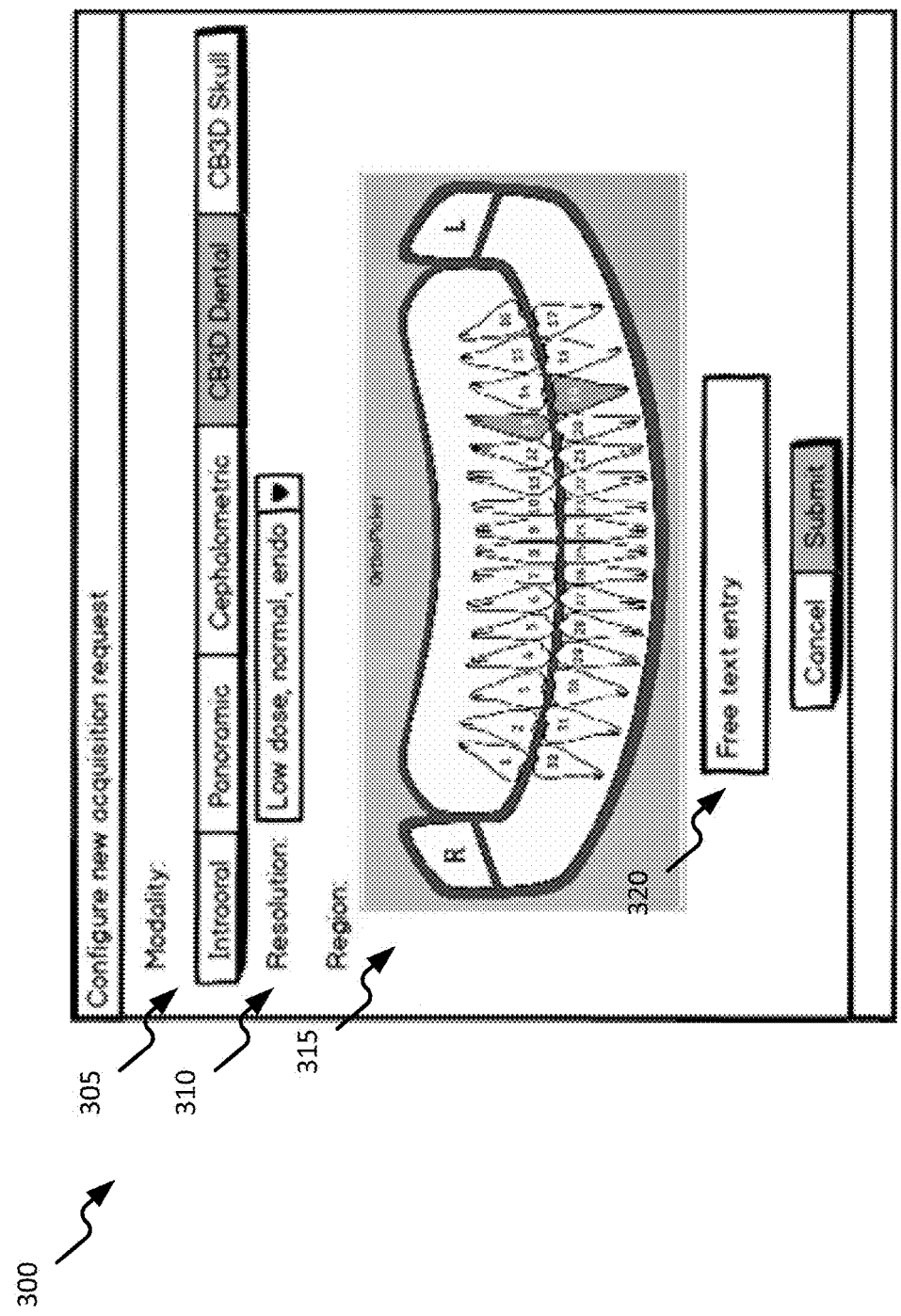
FIG. 3 illustrates a scan request page of a graphical user-interface for use with the system of FIG. 1 according to some embodiments.

FIG. 3 illustrates an exemplary scan request page 300 of a graphical user-interface for initiating a scan request by a user. In some embodiments, the user accesses the scan request page 300 via user-interface 125. In other embodiments, the user accesses the scan request page 300 via a second user-interface through network 130. Scan request 300 may include, among other things, a patient identification (for example, a patient name, a patient identification number, photograph, fingerprint, retinal scan, facial recognition, and/or other biometric data, etc.); a modality selection 305; a resolution selection 310; a region selection 315; and a notes section 320. The modality selection 305 allows the user to select a modality. Although illustrated as including an intraoral selection, a panoramic selection, a cephalometric selection, a cone-beam three-dimensional (CB3D) dental selection, and a CB3D skull selection, the modality selection 305 may include additional selections. The resolution selection 310 allows the user to select a resolution of the requested scan. The region selection, or region-of-interest definition, 315 allows the user to select one or more regions of the patient to be included in the scan. For example, the region selection 315 may include defining an anatomic place (for example, from a head area). The regions may include, but are not limited to, a single tooth, a range of teeth, a jaw, both jaws, and a whole dentition and temporomandibular joint (TMJ). Although illustrated as including an image, in other embodiments, region selection 315 may be, or include, a numeral input (for example, a number of a tooth or numbers of teeth), a textural input (for example, a name of a tooth or names of teeth), a voice command, a selection from a list of teeth, or other method of controlling the user-interface. The notes section 320 allows the user to include additional notes within the scan request.

Returning to FIG. 2, the scan request is stored (block 210). In some embodiments, the scan request is stored in memory 115. In other embodiments, the scan request is stored in a memory of a server via network 130. An imaging protocol based on the scan request is then determined (block 215). In some embodiments, the imaging protocol is further based on the type of image capturing device used. The imaging protocol includes, among other things, a field-of-view. In some embodiments, the imaging protocol includes a field-of-view size and a field-of view position. By automatically determining the imaging protocol, system 100 provides a more expedient image capture with higher accuracy over previously-known systems.

Figure 4:
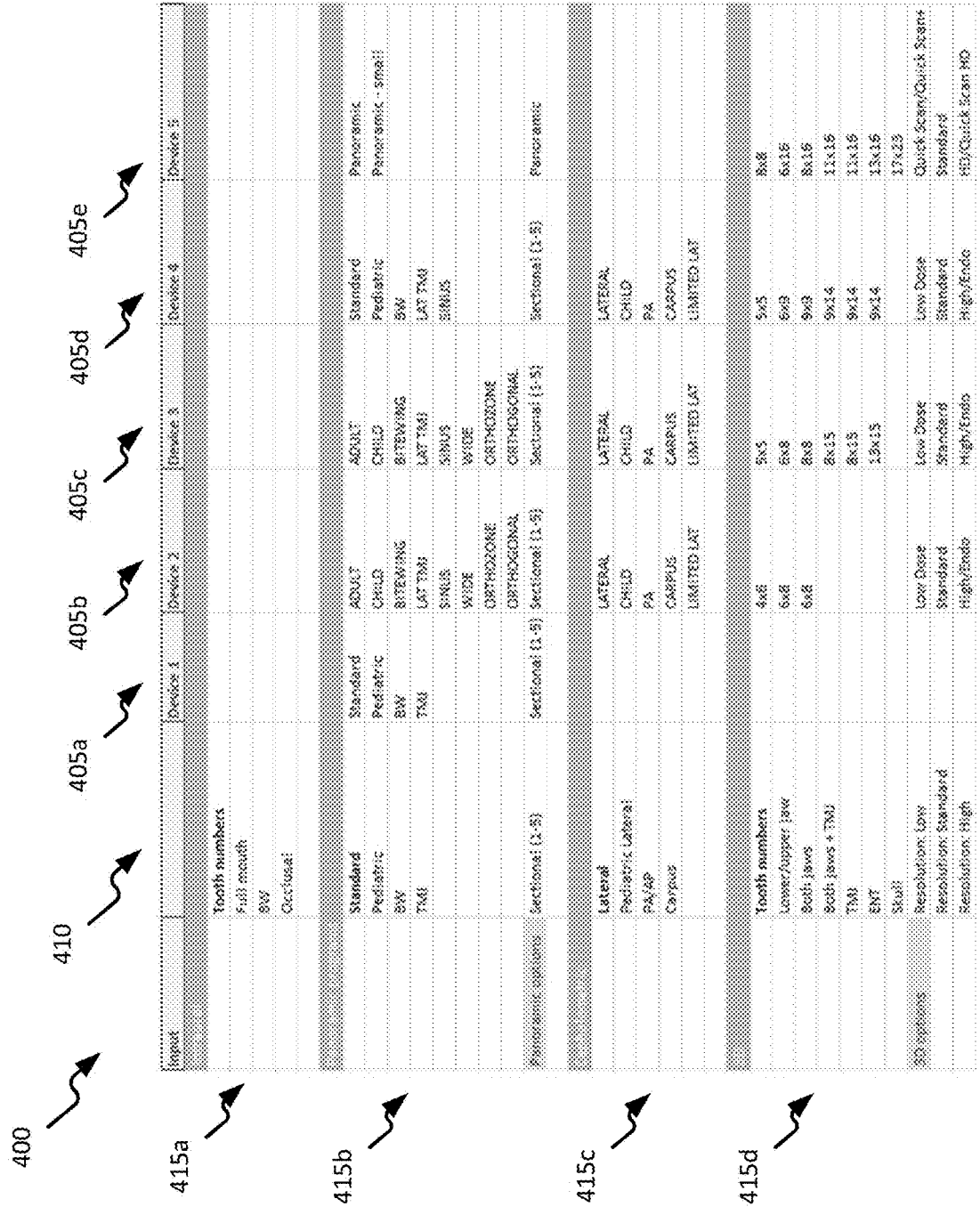
FIG. 4 illustrates a mapping table for use with the system of FIG. 1 according to some embodiments.

FIG. 4 illustrates a mapping table according to some embodiments. In some embodiments, the field-of-view and other various image parameters are determined using the mapping table 400. In the illustrated embodiments, mapping table 400 includes a plurality of device columns 405a-405e corresponding to a plurality of image capturing devices (for example, image capture device 120). The mapping table 400 further includes a selection column 410. In the illustrated embodiment, selection column 410 includes a plurality of modality selection sections 415a-415d corresponding to various modalities. In operation, the controller 105 receives a modality selection and a region selection from the scan request. The controller 105 then uses the mapping table 400 to select a corresponding modality selection section (for example, any one of modality selection sections 415a-415d) based on the modality selection of the scan request. Within the corresponding modality selection section, the controller 105 then selects a corresponding region based on the region selection of the scan request. A field-of-view, as well as other image parameters (for example, resolution, image processing parameters, reconstruction algorithm, artifact removal), and/or technique factors (for example, kV, mA, scan time, etc.), may then be determined for a variety of image capturing devices (for example, Device 1, Device 2, etc.) for the selected modality and region. The specific field-of-view, as well as the other image parameters, are then determined based on the type of image capture device used.

Figure 5:
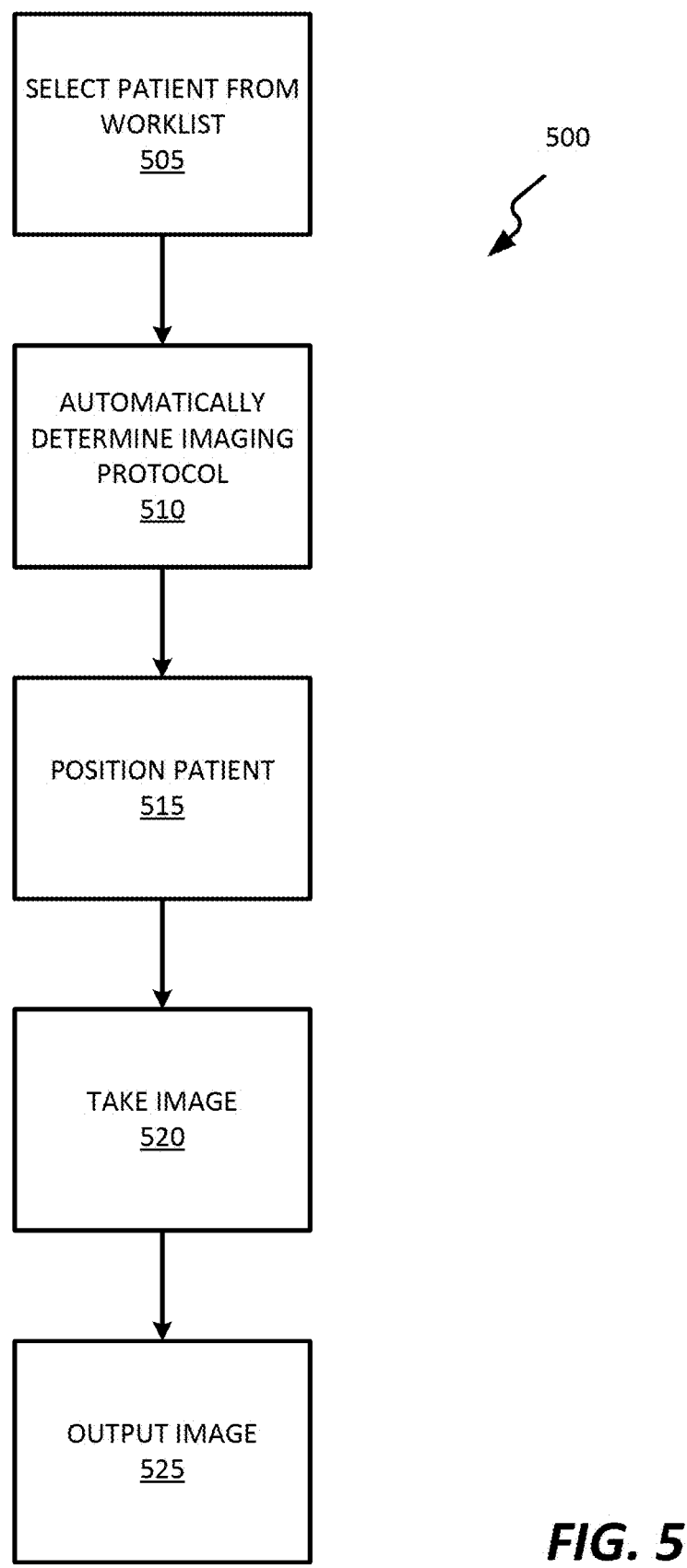
FIG. 5 is a flow chart illustrating a process of the system of FIG. 1 according to some embodiments.

FIG. 5 illustrates a process, or operation, 500 for performing the scan of the patient according to some embodiments. It should be understood that the order of the steps disclosed in process 200 could vary. Although illustrated as occurring in parallel order, in other embodiments, the steps disclosed may be performed in serial order. Furthermore, additional steps may be added to the process and not all of the steps may be required. Process 500 may be performed using the first user-interface 125 and/or the second user-interface 135. The process 500, which refers to scanning the patient (for example, taking an image of the patient) is typically performed using one of the user-interfaces. However, the system may include multiple user-interfaces (for example, the first user-interface 125 can be in multiple dental operatories or treatment rooms). Additionally, in some embodiments, the first user-interface 125 and/or the second user-interface 135 may be a user-interface having no memory requirement for performing the operations described herein.

When the patient is ready to be scanned, a second user (for example, a dental assistant) selects the patient from a worklist (block 505). In some embodiments, the first user and the second user may be the same; while in other embodiments, the first and second users may be different. Additionally, in some embodiments, the first user may be located at a first location, while the second user may be located at a second different location. For example, a dentist located at a first location (for example, a first dentist office) may request a scan to be performed at a second location (for example, a second dentist office or an imaging facility). Additionally, in some embodiments, the first and second locations may be located in different rooms of the same office. In another example, a dentist located at the first location may request a first scan to be performed at the second location and a second scan to be performed at a third location. Additionally, the first user may include more than one users (for example, more than one, or multiple, dentists) using one or more user-interfaces, while the second user may also include more than one users using one or more user-interfaces.

Figure 6:
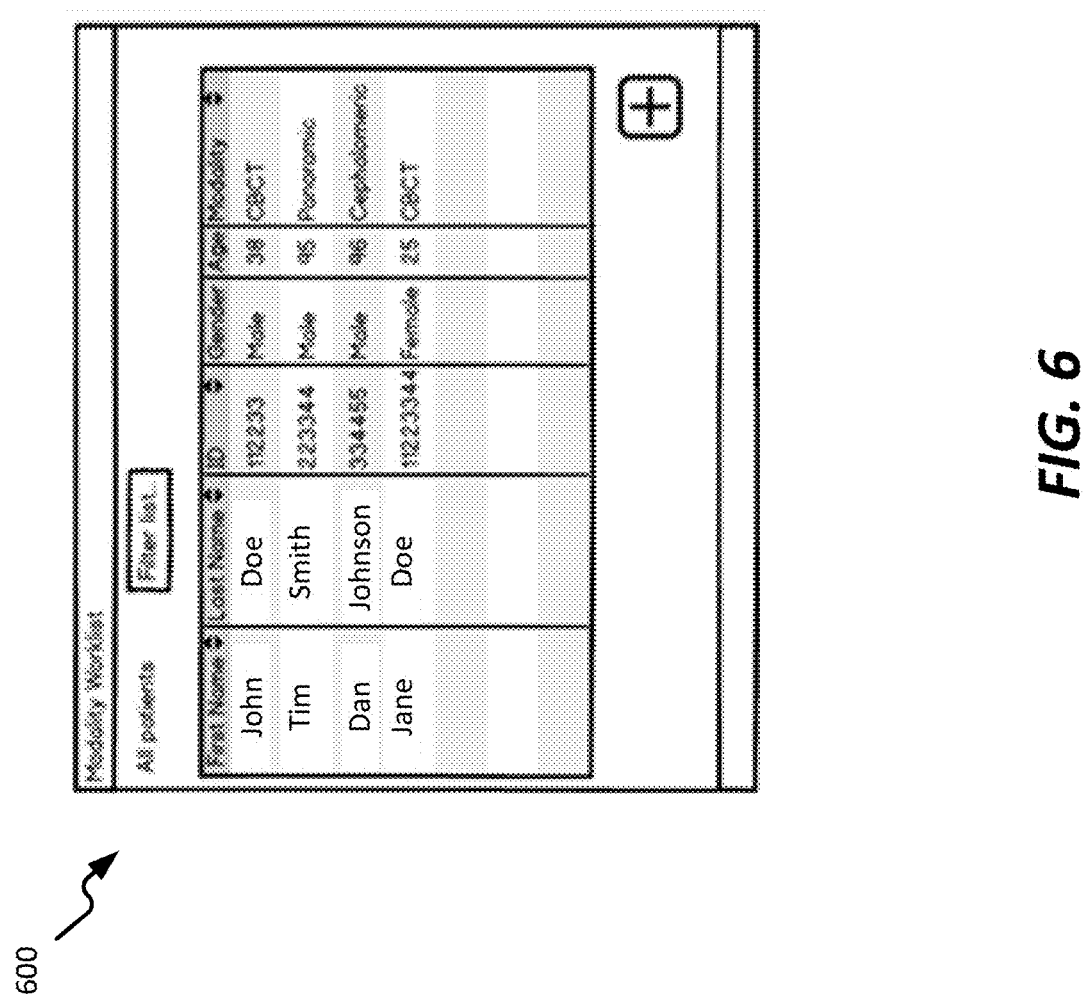
FIG. 6 illustrates a worklist page of a graphical user-interface for use with the system of FIG. 1 according to some embodiments

FIG. 6 illustrates an exemplary worklist page 600 of a graphical user-interface for selecting a patient from a worklist. In the illustrated embodiment, the second user selects the patient to be scanned from the worklist page 600. The worklist page may include one or more patients as well as patient identifying information (for example, name, identification number, gender, age), and selected modality. In some embodiments, the second user may be able to filter the patients using filters or text searching. In another embodiment, the second user may identify the patient, for example, by scanning an identity card containing a barcode or electronic memory. In yet another embodiment, the patient may be identified based on biometric data (for example, fingerprint, retinal scan, and/or facial recognition).

Returning to FIG. 5, once a patient is selected, the imaging protocol is set automatically (block 510). As discussed above, the imaging protocol may be set (for example, using the mapping table 400) based on the scan request, as well as the image capturing device 120 being used to scan the patient. In some embodiments, in addition to or instead of the mapping table, other means or algorithms may be used for selecting the scan protocol and/or scan parameters. For example, fuzzy logic, artificial intelligence (AI) algorithms, and/or machine learning algorithms. In some embodiments, the previously-determined imaging protocol overrides any default settings of the image capturing device 120. In some embodiments, the second user may make additions and/or changes to the image capture beyond the previously-determined imaging protocol (for example, changes to an exposure value, technique factors, etc.). The second user then positions the patient to the image capturing device 120 and/or otherwise prepares the patient to be ready for taking the image or images (block 515). The image is taken by the image capturing device 120 (block 520). In some embodiments, before the image is taken, a scout, or preview, image may be displayed to the second user. In such an embodiment, based on the scout image, the user can see if there is a need for any changes to the image parameters or field-of-view. The image is then output (block 525). In some embodiments, the image is output and stored in memory 115.

Thus, embodiments provide, among other things, a system and method for automatically determining an imaging protocol for an imaging device. Various features and advantages of the invention are set forth in the following claims.

What is claimed is:

1. A method of automatically determining an imaging protocol, the method comprising:
   receiving, via a user-interface, a dental imaging scan request including a region- of-interest definition and a modality selection;
   determining, via a controller and based on the scan request and a type of imaging device to be used, an imaging protocol that includes a field-of-view;
   automatically setting the field-of-view based on the type of imaging device to be used and the region-of-interest definition, wherein the field-of-view includes at least one selected from a group consisting of a field-of-view size and a field-of-view position; and
   performing, via an imaging device of the type of imaging device to be used, a scan of a patient based on the imaging protocol.

2. The method of claim 1, wherein the region-of-interest definition includes at least one selected from a group consisting of a single tooth, a range of teeth, a jaw, both jaws, and a whole dentition and temporomandibular joint (TMJ).

3. The method of claim 1, wherein the user-interface is located at a first location.

4. The method of claim 3, wherein the imaging device is located at a second location.

5. The method of claim 1, wherein the user-interface, controller, and imaging device are communicatively coupled to one another via a network.

6. The method of claim 1, further comprising receiving a patient selection.

7. The method of claim 6, wherein the step of receiving the patient selection is performed via a second user-interface.

8. The method of claim 7, wherein the user-interface and the second user-interface are the same.

9. The method of claim 1, wherein the step of determining, via the controller, the imaging protocol based on the scan request includes determining at least one selected from a group consisting of an image parameter and a technique factor.

10. The method of claim 1, wherein the region-of-interest definition includes at least one selected from a group consisting of a name of a tooth, a number of a tooth, a selection from a list, and an input from a user.

11. The method of claim 1, wherein the field-of-view is automatically set using a mapping table.

12. The method of claim 1, wherein the user-interface includes a worklist having patient identifying data and a modality selection.

13. An imaging system comprising:
   a user-interface;
   a controller including a processor and a memory, the controller configured to
      receive, from the user-interface, a dental imaging scan request including a region-of-interest definition and a modality selection, and
      determine an imaging protocol that includes a field-of-view, the determination based on the scan request and a type of imaging device to be used;
      automatically set the field-of-view based on the type of imaging device to be used and the region-of-interest definition, wherein the field-of-view includes at least one selected from a group consisting of a field-of-view size and a field-of-view position; and
   an imaging device of the type of imaging device to be used configured to perform a scan of a patient based on the imaging protocol.

14. The imaging system of claim 13, wherein the region-of-interest definition including at least one selected from a group consisting of a single tooth, a range of teeth, a jaw, both jaws, and a whole dentition and temporomandibular joint (TMJ).

15. The imaging system of claim 13, wherein the user-interface is located at a first location.

16. The imaging system of claim 15, wherein the imaging device is located at a second location.

17. The imaging system of claim 13, further comprising a network configured to provide a connection between the user-interface, controller, and imaging device.

18. The imaging system of claim 13, wherein the controller is further configured to receive a patient selection.

19. The imaging system of claim 18, further comprising a second user-interface configured to receive the patient selection.

20. The imaging system of claim 13, wherein the controller determining the imaging protocol based on the scan request includes determining at least one selected from a group consisting of an image parameter and a technique factor.

21. The imaging system of claim 13, wherein the region-of-interest definition includes at least one selected from a group consisting of a name of a tooth, a number of a tooth, a selection from a list, and an input from a user.

* * * * *